(12) United States Patent
Zhou et al.

(10) Patent No.: US 9,018,506 B1
(45) Date of Patent: Apr. 28, 2015

(54) SYSTEM AND METHOD FOR CREATING AUDIBLE SOUND REPRESENTATIONS OF ATOMS AND MOLECULES

(71) Applicants: Charles Jianping Zhou, Mountain View, CA (US); Amy Haixia Kang, Mountain View, CA (US)

(72) Inventors: Charles Jianping Zhou, Mountain View, CA (US); Amy Haixia Kang, Mountain View, CA (US)

(*) Notice: Subject to any disclaimer, the term of this patent is extended or adjusted under 35 U.S.C. 154(b) by 0 days.

(21) Appl. No.: 14/517,429

(22) Filed: Oct. 17, 2014

Related U.S. Application Data (60) Provisional application No. 61/904,327, filed on Nov. 14, 2013.

(51) Int. Cl.
| | |
|---|---|
| *G10H 1/38* | (2006.01) |
| *G10H 7/00* | (2006.01) |
| *G10H 1/36* | (2006.01) |
| *C12N 13/00* | (2006.01) |
| *C12P 21/02* | (2006.01) |
| *A61K 41/00* | (2006.01) |

(52) U.S. Cl.
CPC . *G10H 1/38* (2013.01); *G10H 1/36* (2013.01); *C12N 13/00* (2013.01); *C12P 21/02* (2013.01); *A61K 41/0004* (2013.01)

(58) Field of Classification Search
CPC ......... G06F 19/22; G06F 19/28; G06F 19/24; G06F 19/26
USPC .......................................................... 84/613
See application file for complete search history.

(56) References Cited

U.S. PATENT DOCUMENTS

| | | | | |
|---|---|---|---|---|
| 5,689,078 | A | * | 11/1997 | McClard .......................... 84/600 |
| 6,137,042 | A | * | 10/2000 | Kurtzberg et al. .......... 84/477 R |
| 6,332,138 | B1 | * | 12/2001 | Hull et al. ...................... 707/741 |
| 6,930,235 | B2 | * | 8/2005 | Sandborn et al. ............. 84/483.2 |
| 7,179,979 | B2 | * | 2/2007 | Howarth et al. .............. 84/483.2 |
| 7,629,528 | B2 | * | 12/2009 | Childs et al. .................... 84/609 |
| 7,838,757 | B2 | * | 11/2010 | Howarth et al. ................ 84/619 |
| 8,183,451 | B1 | * | 5/2012 | Panaiotis ......................... 84/601 |
| 8,874,243 | B2 | * | 10/2014 | Bennett et al. ................... 700/92 |
| 2002/0176591 | A1 | * | 11/2002 | Sandborn et al. ............. 381/118 |
| 2002/0177186 | A1 | | 11/2002 | Sternheimer |
| 2006/0236845 | A1 | * | 10/2006 | Kilkis ............................. 84/600 |
| 2008/0081319 | A1 | * | 4/2008 | Dunlop ......................... 434/106 |
| 2010/0204540 | A1 | * | 8/2010 | Oohashi et al. ................. 600/27 |

OTHER PUBLICATIONS

Sumo, A Sonification Utility for Molecules, Grond, Florian et al., Proceedings of the 14th International Conference on Auditory Display, Paris, France, Jun. 24-27, 2008, 7 pages.*

(Continued)

*Primary Examiner* — Jeffrey Donels
(74) *Attorney, Agent, or Firm* — Plager Schack LLP

(57) ABSTRACT

System and method creates audible sound representations for atoms and molecules. Musical notes or musical note combinations (chords) are assigned to each element in elemental periodic table. Musical notes or musical note combinations (chords) are assigned to atomic and molecular bonds (covalent and ionic, intra and inter molecular interactions) and to all molecular functional groups. This invention creates a new representation format, the audible sound format, for atoms and molecules in addition to text and image formats currently used in schools, universities, research institutes and industries, etc.

10 Claims, 5 Drawing Sheets

| ATOM | Sc | Ti | V | Cr | Mn |
|---|---|---|---|---|---|
| MUSIC NOTE | A#0 29.1Hz | B0 30.9Hz | C1 32.7Hz | C#1 3465Hz | D1 36.71Hz |
| ATOM | Y | Zr | Nb | Mo | Tc |
| MUSIC NOTE | G#1 51.9Hz | A1 55Hz | B1 61.7Hz | C2 65.4Hz | C#2 69.3Hz |
| ATOM | La-Lu | Hf | Ta | W | Re |
| MUSIC NOTE | | G2 98Hz | G6 1568Hz | G#6 1661Hz | C#7 2217Hz |
| ATOM | Ac-Lr | | | | |
| MUSIC NOTE | | | | | |

| ATOM | Fe | Co | Ni | Cu | Zn |
|---|---|---|---|---|---|
| MUSIC NOTE | D#1 38.9Hz | E1 41.2Hz | F1 43.7Hz | F#1 46.3Hz | G 49Hz |
| ATOM | Ru | Rh | Pd | Ag | Cd |
| MUSIC NOTE | D2 73.4Hz | D#2 77.8Hz | E2 82.4Hz | F2 87.3Hz | F#2 92.5Hz |
| ATOM | Os | Ir | Pt | Au | Hg |
| MUSIC NOTE | D#7 2489Hz | F#7 2960Hz | G 3136Hz | G#7 3322Hz | B7 3951Hz |
| ATOM | | | | | |
| MUSIC NOTE | | | | | |

(56) References Cited

OTHER PUBLICATIONS

Molecular Music: The Acoustic Conversion of Molecular Vibrational Spectra, Delatour, Thierry; Computer Music Journal 24:3, pp, 48-68, Fall 2000.*

Delatour, "The Acoustic Conversion of Molecular Vibrational Spectra, Computer Music Journal." 24:3, pp. 48-68, Fall 2000 pp. 49, 51, 68 [Online] URL=<http://dl.acm.org/citation.cfm?id+1115925>.

Leveau et al., "Instrument-Specific Harmonic Atoms for Mid-Level Music Representation." IEEE Transactions on Audio, Speech, and Language Processing. vol. 16, No. 1, Jan. 2008, Entire document [online] URL=<https://www.institut-langevin.espci.fr/IMG/pdf/Leveau_TSALP08.pdf>.

Shi et al., "Electronic Music for Bio-Molecules Using Short Music Phrases." vol. 40, No. 2, pp. 137-141, 2007, Entire document [online] URL=<http://www.mitpressjournals.org/doi/abs/10.1162/leon.2007.40.2.137>.

* cited by examiner

FIG.1

| | 0 | 1 | 2 | 3 | 4 | 5 | 6 | 7 | 8 |
|---|---|---|---|---|---|---|---|---|---|
| C | 16.35 | 32.7 | 65.41 | 103.8 | 261.6 | 523.3 | 1047 | 2093 | 4186 |
| C# | 17.32 | 34.65 | 69.3 | 138.6 | 277.2 | 554.4 | 1109 | 2217 | 4435 |
| D | 18.35 | 36.71 | 73.42 | 146.8 | 293.7 | 587.3 | 1175 | 2349 | 4699 |
| Eb | 19.45 | 38.89 | 77.78 | 155.6 | 311.1 | 622.3 | 1245 | 2489 | 4978 |
| E | 20.6 | 41.2 | 82.41 | 164.8 | 329.6 | 659.3 | 1319 | 2637 | 5274 |
| F | 21.83 | 43.65 | 87.31 | 174.6 | 349.2 | 698.5 | 1397 | 2794 | 5588 |
| F# | 23.12 | 46.25 | 92.5 | 185 | 370 | 740 | 1480 | 2960 | 5920 |
| G | 24.5 | 49 | 98 | 196 | 393 | 784 | 1568 | 3136 | 6272 |
| G# | 25.96 | 51.91 | 103.8 | 207.7 | 415.3 | 830.6 | 1661 | 3322 | 6645 |
| A | 27.5 | 55 | 110 | 220 | 440 | 880 | 1760 | 3520 | 7040 |
| Bb | 29.14 | 58.27 | 116.5 | 233.1 | 466.2 | 932.3 | 1865 | 3729 | 7459 |
| B | 30.87 | 61.74 | 123.5 | 246.9 | 493.9 | 987.8 | 1976 | 3951 | 7902 |

FIG.2

| ATOM | H | | Be | | B | C | N | O | F | He |
|---|---|---|---|---|---|---|---|---|---|---|
| MUSIC NOTE | A3 220Hz | | A#2 116.5Hz | | B2 123.5Hz | C4 261.6Hz | D4 293.7Hz | E4 329.6Hz | F3 174.6Hz | C#8 4435Hz |
| ATOM | Li | | Mg | | Al | Si | P | S | Cl | Ne |
| MUSIC NOTE | A4 440Hz | | A#3 223.1Hz | | B3 246.9Hz | C5 523.3Hz | D5 587.3Hz | E5 659.3Hz | F4 349.2Hz | D#8 4978Hz |
| ATOM | Na | | Ca | | Ga | Ge | As | Se | Br | Ar |
| MUSIC NOTE | A5 880Hz | | A#4 466.2Hz | | B4 493.9Hz | C6 1047Hz | D6 1175Hz | E6 1319Hz | F5 698.5Hz | F8 5588Hz |
| ATOM | K | | Sr | | In | SN | Sb | Te | I | Kr |
| MUSIC NOTE | A6 1760Hz | | A#5 932.3Hz | | B5 987.8Hz | C7 2093Hz | D7 2349Hz | E7 2637Hz | F6 1397Hz | F#8 5920Hz |
| ATOM | Rb | | Ba | | Tl | Pb | Bi | Po | At | Xe |
| MUSIC NOTE | A7 3520Hz | | A#6 1865Hz | | B6 1796Hz | C8 4186Hz | D8 4699Hz | E8 5274Hz | F7 2794Hz | G8 6272Hz |
| ATOM | Cs | | Ra | | | | | | | Rn |
| MUSIC NOTE | A8 7040Hz | | A#7 3729Hz | | | | | | | G#8 6645Hz |
| ATOM | Fr | | | | | | | | | |
| MUSIC NOTE | A0 27.5Hz | | | | | | | | | |

FIG.3

| ATOM | Sc | Ti | V | Cr | Mn |
|---|---|---|---|---|---|
| MUSIC NOTE | A#0 29.1Hz | B0 30.9Hz | C1 32.7Hz | C#1 3465Hz | D1 36.71Hz |
| ATOM | Y | Zr | Nb | Mo | Tc |
| MUSIC NOTE | G#1 51.9Hz | A1 55Hz | B1 61.7Hz | C2 65.4Hz | C#2 69.3Hz |
| ATOM | La-Lu | Hf | Ta | W | Re |
| MUSIC NOTE | | G2 98Hz | G6 1568Hz | G#6 1661Hz | C#7 2217Hz |
| ATOM | Ac-Lr | | | | |
| MUSIC NOTE | | | | | |

| ATOM | Fe | Co | Ni | Cu | Zn |
|---|---|---|---|---|---|
| MUSIC NOTE | D#1 38.9Hz | E1 41.2Hz | F1 43.7Hz | F#1 46.3Hz | G 49Hz |
| ATOM | Ru | Rh | Pd | Ag | Cd |
| MUSIC NOTE | D2 73.4Hz | D#2 77.8Hz | E2 82.4Hz | F2 87.3Hz | F#2 92.5Hz |
| ATOM | Os | Ir | Pt | Au | Hg |
| MUSIC NOTE | D#7 2489Hz | F#7 2960Hz | G 3136Hz | G#7 3322Hz | B7 3951Hz |
| ATOM | | | | | |
| MUSIC NOTE | | | | | |

SYSTEM AND METHOD FOR CREATING AUDIBLE SOUND REPRESENTATIONS OF ATOMS AND MOLECULES

CROSS-REFERENCE TO RELATED APPLICATIONS

This application claims priority to U.S. Provisional Patent Application 61/904,327, filed Nov. 14, 2013, the entirety of which is incorporated herein by reference.

BACKGROUND OF THE INVENTION

1. Field of the Invention

The present invention relates to a data analysis system and more particularly to a system for analyzing data to generate narrative content.

2. Description of the Related Art

Currently there are two basic formats for representations of atoms and molecules. First, is the text representation, which uses human readable words to describe atoms and molecules. Systematic or common molecular names and structure formula are examples in this format. Second, is the image representation, which uses drawing to describe atoms and molecule via human visualization.

It is known that atoms and molecules are in constant vibration. Every atom or molecule has its own vibrational energy levels that can be detected and displayed by analytical instruments, but the vibrational frequencies are not at ranges that human can hear (20 to 20 kHz).

BRIEF SUMMARY OF THE INVENTION

Embodiments of the present invention address deficiencies of the art in respect to providing a representation of the vibrational energy levels of atoms and molecules that is discernable to the human ear (i.e. the representations correspond to frequencies within the 2 kHz to 20 kHz range for human hearing). Embodiments of a system and method maps atoms and molecules to music notes or note combinations (chords) that are audible to human ear. The systematic and common names for molecules or structural formula of all molecules are automatically translated into music note format, by following rules disclosed herein. In addition, a computer software tool has been created for converting IUPAC International Chemical Identifier ("InChI") or Simplified Molecular-Input Line-Entry System directly into audible sound format. The created sound and/or music files for atoms and molecules are played using the software tool in computers, or any other electronic music device.

Embodiments of the present invention map atoms and molecules to music notes and music notes combinations to create educational products in software and electronic hardware formats. In addition, these mappings may be used to produce security devices or fire alarms as the mappings can identify the presence of CO, CO2, or other hazardous chemicals, which will alert people with specific information and allow them to take special measures. The mappings can be used in environmental monitoring to identify various chemicals though sound analysis. Also, these mappings can be integrated into gaming systems and provide natural sounds, for example, for use in educational chemistry games. Also, data mining systems may use these methods to analyze large amounts of data and provide sound pattern analysis by create similar music mapping. Finally, the mappings may be used in a simple musical instrument, such as a music toy.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Atoms and molecules have vibrational energy levels, which are detectable by analytical instruments, but the frequencies are not in audible ranges (20 to 20 kHz) that human can hear. An embodiment of the present invention provides for a system and method to map music notes or music notes combinations (chords) to atoms and molecules, to create sounds and music for atoms and molecules that are audible to the human ear.

There are many music scales and modes that have evolved over the history of human civilizations. One of the methods described in this invention is based on a chromatic scale with twelve pitches, each a semitone above or below another. On a modern piano or other equal-tempered instrument, all the semitones are the same size (100 cents), which are widely used in contemporary music. An embodiment of the present invention uses one of the popular musical scales, but it is not limited to just one music scale and mode. Many musical scales and modes can be used for this invention, but the basic concept and methodology of mapping music notes or music notes combinations (chords) to atoms, or atomic and molecular bonds, or molecular functional groups are the same.

The basic formula for the frequencies of music notes of the equal tempered scale is given by:

$$fn = f0*(a)^n \text{ where}$$

f0=the frequency of one fixed note which must be defined (a common choice is setting the A above middle C (A4) at f0=440 Hz).

n=the number of half steps away from the fixed note. If it is at a higher note, n is positive. If it is on a lower note, n is negative.

fn=the frequency of the note n half steps away.

$a=(2)^{1/12}$=the twelfth root of 2=1.059463094359 . . .

The wavelength of the sound for the notes can be found from:

$$Wn=c/fn$$ where

W is the wavelength and c is the speed of sound in the media. The speed of sound depends on the conditions of media, but is approximately 345 m/s in air at room temperature.

Figure 1:
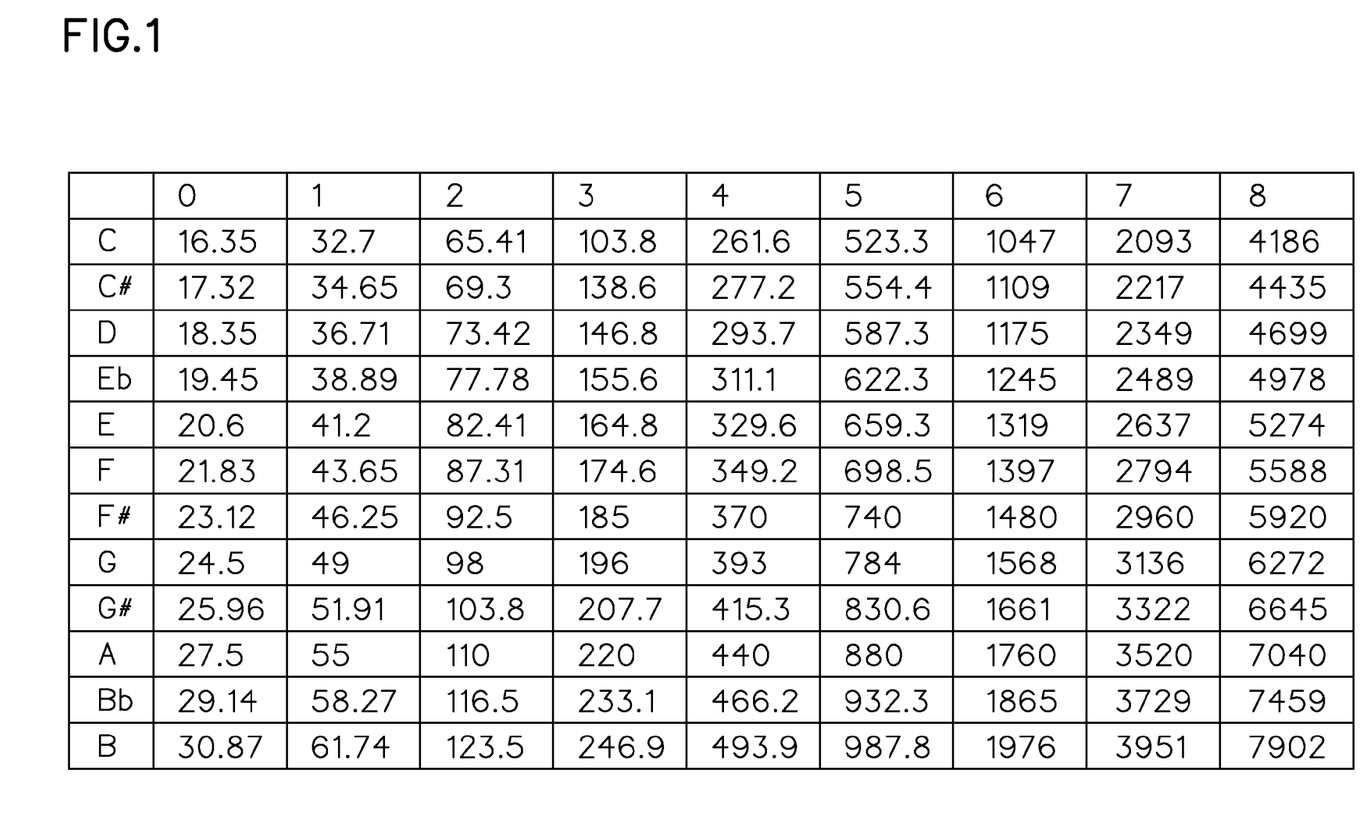
FIG. 1 is a table of the frequencies of musical pitches using an equal tempered scale with A4=440 Hz.

See FIG. 1 for a table of the frequencies of music notes of the equal tempered scale.

From elemental periodic table, there are 78 essentially stable elements and these have atomic numbers 1-42, 44-60, 62-73, and 75-81. The others are radioactive and will decay away. The number of elements might be as high as 126 total predicted by scientists. In order to assign music notes or music notes combinations (chords) to elements, it is necessary to consider the relative importance of all elements. The top 10 elements in the Sun are: H, He, O, C, N, Si, Mg, Ne, Fe, S. The human body requires 24 elements to function properly; and they are listed here: O, C, H, N, Ca, P, S, K, Na, Cl, Mg, Si, Fe, F, Zn, Cu, Mn, Sn, I, Ni, Mo, V, Cr, Co. There are also other factors to be considered regarding to the relative importance of elements such as economic effect, usefulness in daily life, and importance in chemistry, etc. It is understood that there will be many ways to do the music notes and elements mapping. The following is a set of principle rules used in this invention, but it is not limited to only one set of rules, further modified rules can be used as well:

1) Important elements which are used most commonly may be mapped with music notes near or at octave number 4 notes such as: C4 to B4 (see FIG. 1).
2) Elements from same group from the elemental periodic table may be mapped as much as possible in same class of music notes, for example, C, Si, Ge, Sn, Pb, Fl may be mapped with notes within C0 to C8, the intention here is to keep some consistency with the periodic table, and make it easier for people to memorize, but there should not be a limitation for rule modifications (see FIG. 1, 2).
3) For less commonly used or unstable elements, music notes far away from octave number 4 can be used or music notes combinations (chords) can be used.
4) Music notes combinations (chords) are preferably, but not limited to be, used for molecular functional groups. Once the music notes are mapped to elements, it can greatly simplify the conversion process from molecular structural formula to sound format when chords are used.
5) Music Note A4=440 Hz is assigned to hydrogen for its importance as the origin of all elements.
6) Music Note C4=261.6 Hz is assigned to carbon for its importance in life.
7) For chiral centers in molecules, F#7=2960 Hz is assigned to R-config, G#7=3322 Hz is assigned to S-config, G7=3136 Hz is assigned to D-config, Bb7=3729 Hz is assigned to L-config, F#8=5920 Hz is assigned to (+)-, G#8=6645 Hz is assigned to (−)-.
8) For positive charge (+), use C#7=2217 Hz to represent it. For negative charge (−), use B7=3951 Hz to represent it. For a radical, use F#6=1480 Hz to represent.
9) For cyclic ring system, use C#=4435 Hz to denote CC bond breakage point; use G8=6272 Hz to denote heteroatomic bond break point.
10) For inter and intra molecular interaction, use Bb6=1865 Hz to represent it.
11) Mostly 4/4 and 3/4 music meter are used, and quarter (q), eighth (e), sixteenth(s) note values are used, which will be specified in the sound format.

The following are some examples with descriptions on how to do the mapping with the above rules. The chromatic music scale, which has twelve pitches, is used here as example. This invention is not limited to the music scale used here as other musical scales can also be used.

Figure 2:
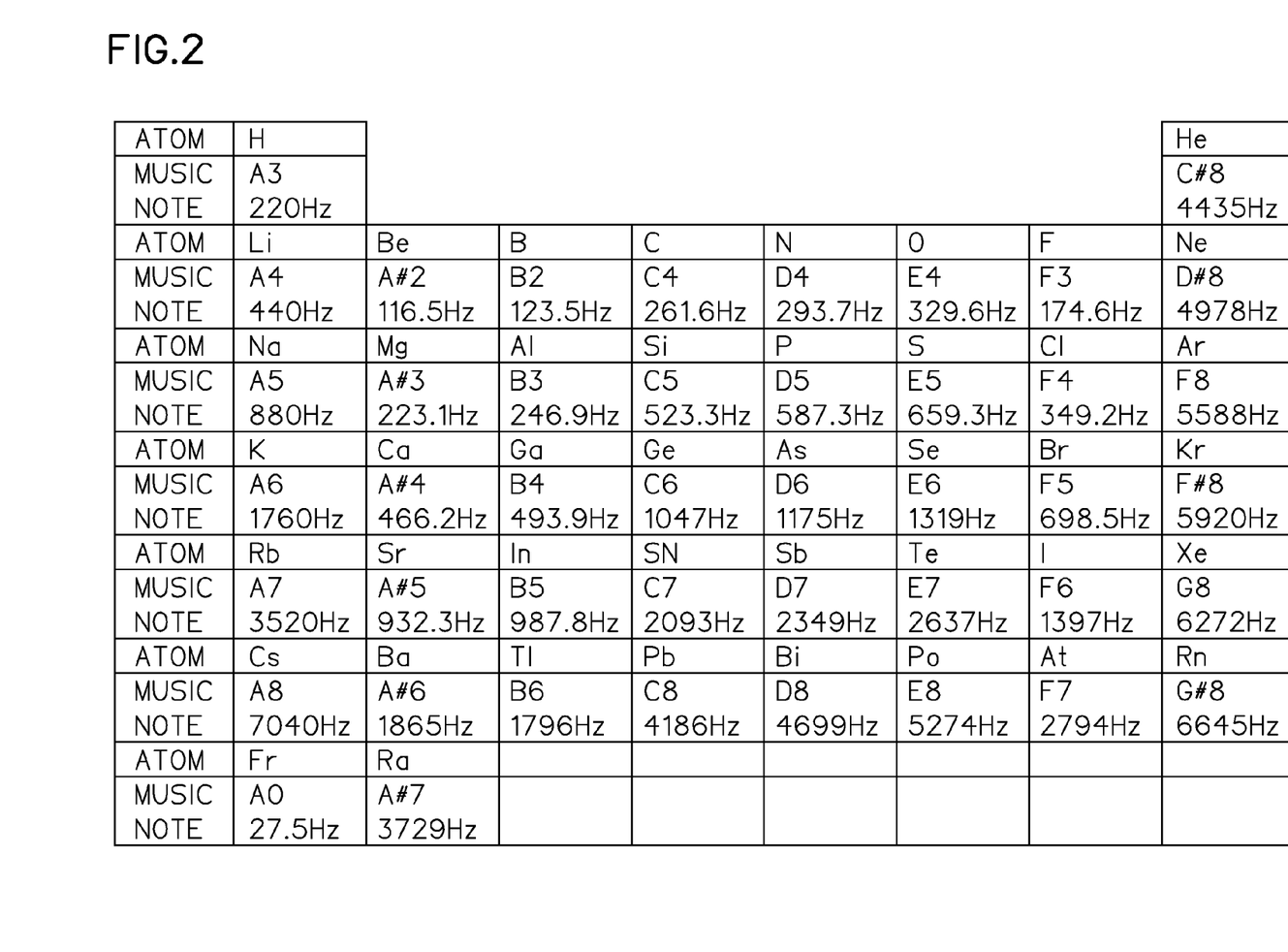
FIG. 2 is a table of music notes and chord assignment to major group elements and most transition metals in an elemental periodic chart.
Figure 3:
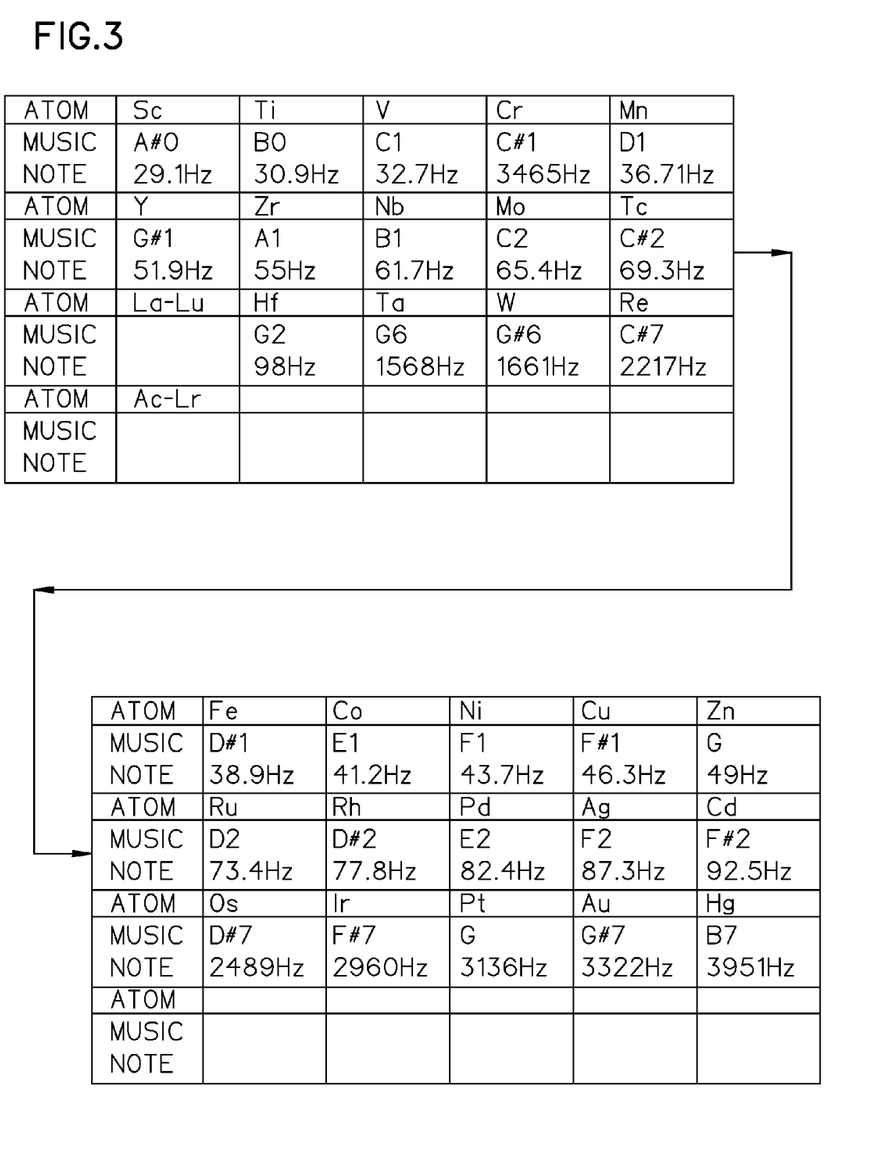
FIG. 3 is an example table of musical notes and chord assignments to most transition metals in an elemental periodic chart, in accordance with an aspect of the present invention.

FIG. 2 shows music notes or musical note combinations (chords) assigned to elements in elemental periodic table. FIG. 3 shows music notes or musical note combinations (chords) assigned to most transition metals in an elemental periodic chart. One example method can be extended to assign different music notes to every element, or it can be extended to assign different musical note combinations (chords) to every element. The goal is to map distinct music notes or music notes combinations (chords) to all elements in the elemental periodic table. In order to get the best sound effect, it is possible that various music notes may be assigned to one element as the starting point, for example, music note 'A' or 'B' or 'C' alone, or in combination, can be assigned to hydrogen atom to get started. As long as the outcome of the sound for each atom or molecule can be differentiated, it is acceptable. This methodology can be repeated to cover all elements in the periodic table.

Based on the music notes or chords assigned to atoms, for simple molecules such as water, oxygen, methane, etc., their structural molecular formula can be directly translated into sheet music (such as "A4q E4q A4q", "E4q E4q", "A4q A4q A4q A4q C4q"), which are readable by human and computer devices, and can be played by computers or on any music instrument.

For small molecules (e.g., molecular weight <=500) with only single atomic bonds, C major scale can be used and starting at C4, each musical note value (i.e. length) can be set to quarter notes. For example: for water molecule: $H_2O$ or HOH. From table in FIG. 2, note A4 is assigned to H atom, and E4 is assigned to O atom, the sound representations for water molecule are: 'A4q A4q E4q' or 'A4q E4q A4q'. "q" denotes quarter note here. Since there are multiple ways to describe any molecule in text format or image format, it is highly desired that there are multiple ways to describe any molecule in sound format. That is, once the music note is assigned to an element, the sequence and the values of the music notes can vary for the same molecule, just as C2H5OH and HOCH2CH3 represent the same molecule-ethanol.

For small molecules (e.g., molecular weight <=500) that contain double or triple atomic bonds (such as C=C, C=O, C=S, C=N, and CC or CN triple bonds), eighth notes and sixteenth notes are used respectively to differentiate from single bonds. For example: CH3CH=CHCCCH3, there are single, double, and triple CC bonds. One of the sound representations for this molecule is: "A4q A4q A4q C4q A4q C4e C4e C4e C4e A4q C4s C4s C4s C4s C4s C4s C4q A4q A4q A4q." "e" denotes eighth note here, and "s" denotes sixteenth note. As stated earlier, this invention is not limited to using one method only to differentiate atomic bonds in molecules. Another method used is to assign chords to double bond when different atoms are involved. For example for CH3COCH3, which contains C=O double bond, the conversion can be: "A4q A4q A4q C4q C4qE4q C4q A4q A4q A4q."

For cyclic molecules, for example, cyclopropane 1CCC1, C atom 1 is the break point, the sound format can be: "A4q A4q C4q C#4q A4q A4q C4q A4q A4q C4q C#4q."

Use F#7, G7, G#7, Bbl, F#8, G#8 to label all chiral atoms in the molecules if needed. For example, use "C4q F#7q" to represent carbon atom with R config.

Use C#7, B7 to label charges in molecules if needed. For example, NaCl can be converted to: "A2q C#7q F5q B7q." Use F#6 to label radicals, for example, HO radical can be represented as: "A4q E4q F#6q."

For molecules with molecular weight >500, a combination of methods described previously is used. Musical time signatures and note sequences are created via a graph structured, layered approach to reflect the complexity of the molecular structure: (a) map the sequence of atoms in a molecular structure formula, see also FIGS. 1 and 2 for musical notes assignments; (b) map chemical bond types: single bonding, double bonding, triple bonding, atomic charges, see also steps previously described; (c) for big molecules (such as, but not limited to polymers), the created sound and/or music format can be fine tuned using intra and inter molecular interactions. Chords may be used more extensively to simplify the repeated unites, motifs and domains. The force of the notes can also be made proportional to, but not limited to, the bond strength measured or calculated.

Music notes or musical note combinations (chords) may be assigned to all molecular functional groups and atomic bonds (covalent or ionic), such as the following but not limited to the following: Na+Cl—, C—C bond, C=C bond, CC, CN, CX triple bonds, C=O bonds, C—OH bond, ketone functional group, alcohol functional group, amine functional group, amide functional group, ester functional group, C—N bond, —CN group, C—S bond, —CS group, ether group, hydrocarbon functional groups (hydrocarbyls), carbocations, carbanions, cations, anions, radicals, groups containing oxygen, groups containing halogens, groups containing nitrogen, groups containing sulfur, groups containing phosphorus, groups containing boron, groups containing metals, inter and intra-hydrogen bonding, etc.

Figure 4:
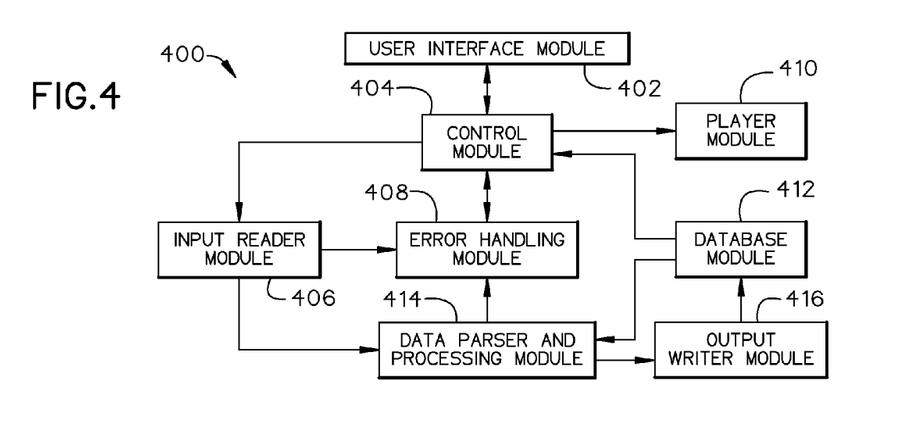
FIG. 4 is a flow diagram illustrating an example device structure and method of operation in accordance with an aspect of the present invention.
Figure 5:
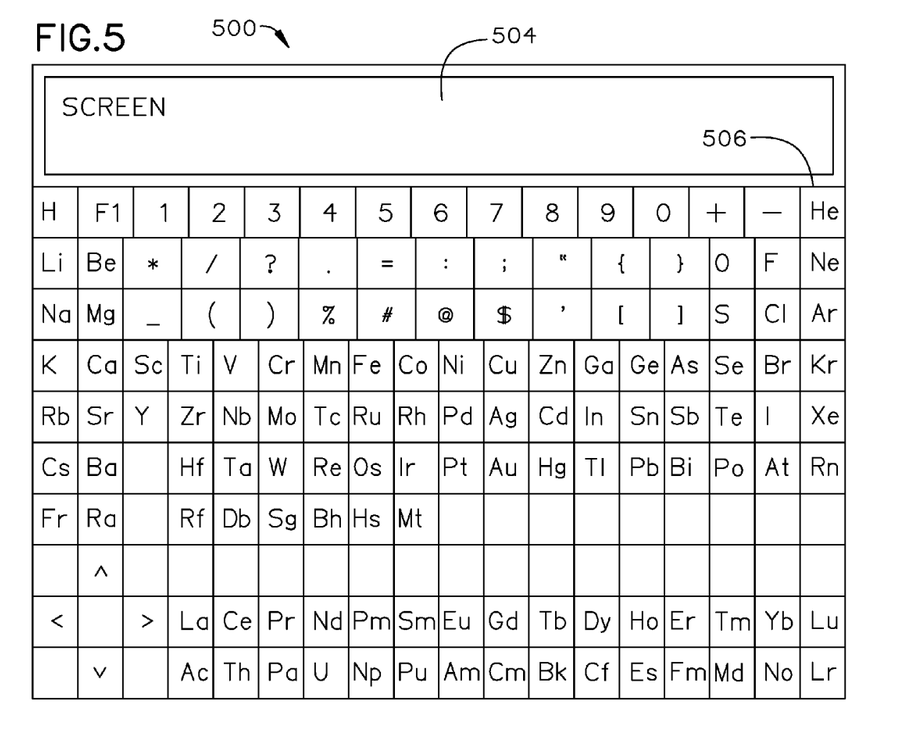
FIG. 5 is a top view of an example standalone electronic musical device in accordance with an aspect of the present invention.

Referring now to FIG. 4, a flow diagram is provided to illustrate how the components 400 of the electronic music device 500 shown in FIG. 5 interrelate. The user interface (UI) module 402 has multiple user interfaces: web based (WUI), standalone graphic user interface (GUI), and command line interface (CLI). The UI module 402 is the place for a user to input data and make selections. For example, a user can select a molecule to generate sound or music if the molecule has no sound or music already made or the user simply wanted to create another sound or music format for the molecule. A user can also select to play the sounds or music for molecules that already have sounds or music stored in the database module 412. The UI module 402 directly interacts with control module 404 to provide user instructions. The UI module 402 contains menu subroutines to pass user instructions to the control module 404, and displays task status to the user.

The control module 404 is a harness-like control center that delegates tasks to other modules, and also does database management if the user is an administrator who has special privilege to access of databases. The control module 404 takes instructions from the UI module 402 and interacts directly with the input reader module 406, the error handling module 408, the player module 410 and the database module 412.

The input reader module 406 handles all the input data collected from atoms and molecules, using standard molecular structural formats, including but not limited to, IUPAC International Chemical Identifier (InChI) and Simplified Molecular-Input Line-Entry System or SMILES, etc. The input reader module 406 takes instructions from the control module 402 and directly interacts with the data parser and processing module 414 and the error handling module 408. If the input formats are correct, the data will go to the data parser and processing module 414, otherwise and error is passed to the error handling module 408. The data parser and processing module 414 takes data from the input reader module 406, passes any found errors to the error handling module 408, fetches rules input from the database module 412, process the data based on the rule and passes processed data to the output writer module 416. Both the input reader module 406 and the data parser and processing module 414 have logic gates such that if an error is found, the error goes to the error handling module 408, and if no error, go to the next module.

The output writer module 416 takes processed data from the data parser and processing module 414 and writes output data in the correct sound and music format to the database module 412. The player module 410 takes user instructions from the control module 404 and takes action to play music files passed via the control module 404 which is fetched from database module 412.

The error handling module 408 takes error messages from the input reader module 406 and the data parser and processing module 414 and reports status to the control module 404. The error handling module 408 has both logic gates and subroutines to handle errors: repair if possible, otherwise report error and take action according rule sets.

The database module 412 contains all the rules, data and knowledge databases and is managed via the control module 404 by user with admin privileges. The database module 412 provides rule information to the data parser and processing module 414 and takes output data from the output writer module 416.

Figure 6:
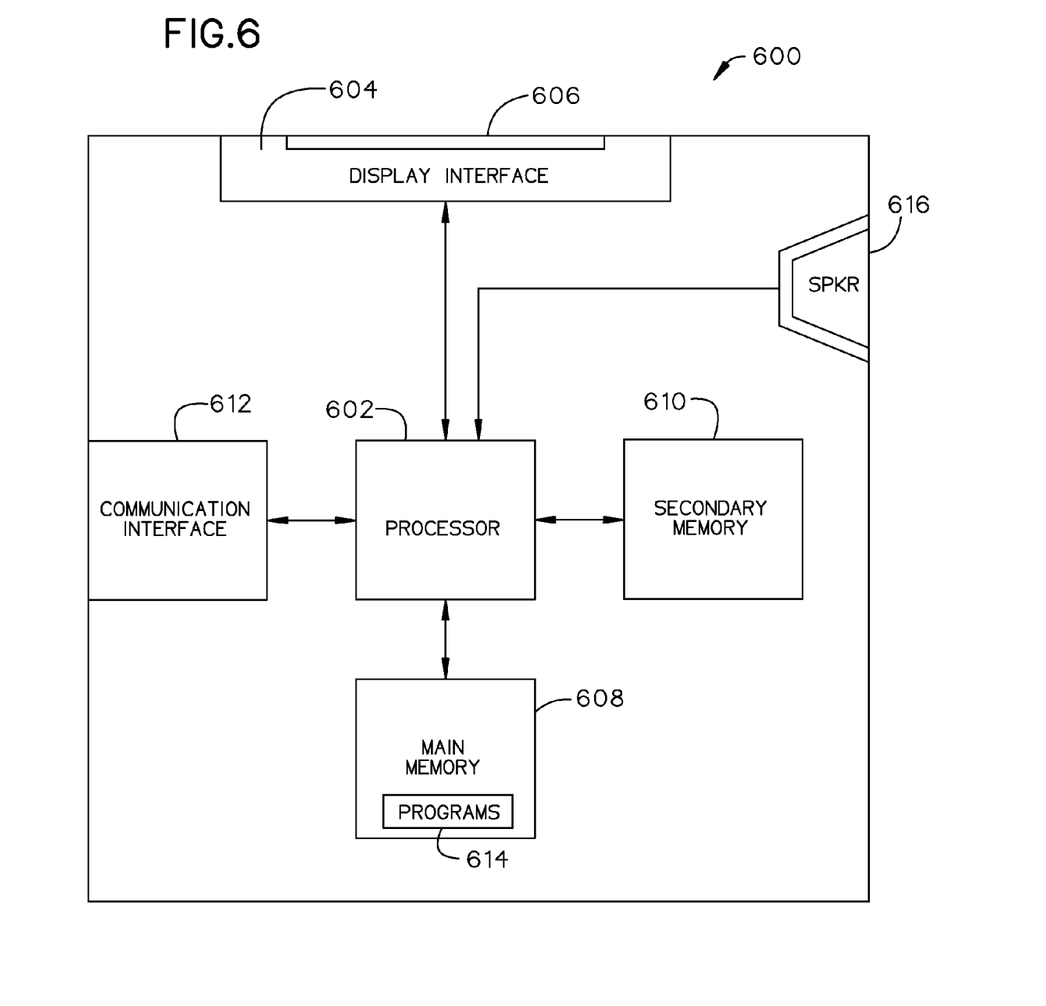
FIG. 6 is a block diagram of the example standalone electronic musical device of FIG. 5.

Turning to FIG. 5, an example electronic music device 500 may include a display screen 504 to provide the user with feedback and instructions, as well as a customized keyboard 506 having dedicated keys for each chemical element. One embodiment of hardware components to implement an electronic music device 600 is shown in FIG. 6. A processor 602 executes computer instructions from programs 614 stored in main memory 608 and secondary memory 610. The processor 602 sends visual information to a display interface 604 to be displayed on a display 606 to a user. Additionally, the processor 602 sends audio information to information to a speaker 616 to play sounds and or music representing a chemical element or molecule. The processor 602 may also be coupled to a communication interface 612 for sending data to and receiving data from other devices via a local connection or through a networked connection.

One embodiment of the present invention can be extended, but not limited to, security devices or fire alarms. For example, it can identify and produce different sounds for CO and CO2, or other hazardous chemicals, which will alert and inform fire fighters or general public with specific information regarding hazards, and take special measures based on the sound of molecules. One embodiment may also be used in environmental monitoring for identifying various chemicals from analytical instruments, and then inform people through sound. Additionally, aspects of the present invention can be integrated in gaming systems and provide sounds for educational chemistry games to educate students by playing games. An embodiment of the present invention can be made into chemical data mining system to analyze large amount chemical data and provide pattern analysis by using similar music notes mapping method to data unit. An aspect of the present invention can also be used in chemistry education for general public and especially for the vision-impaired.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Having thus described the invention of the present application in detail and by reference to embodiments thereof, it will be apparent that modifications and variations are possible without departing from the scope of the invention defined in the appended claims as follows:

We claim:

1. A method of playing a representation of a molecule on an electronic musical device, the method comprising:
   mapping each element of a molecule to a musical note;
   determining a value of each musical note based upon a type of molecular bond between elements;
   arranging the musical notes in a sequence; and
   playing the sequence of musical notes through a speaker of the electronic musical device.

2. The method of claim 1, wherein the mapping is based on a chromatic scale having twelve pitches, each pitch being a semitone above or below another pitch.

3. The method of claim 1, wherein the musical notes are mapped to the elements based on a relative importance of each element of the molecule, wherein the relative importance corresponds to at least one of a quantity of the element in the molecule and a need for the element in the molecule.

4. The method of claim 3, wherein elements which are used most commonly are mapped to music notes near or at notes of a middle octave of an equal-tempered scale.

5. The method of claim 1, wherein a particular molecular combination is mapped to a chord.

6. The method of claim 1, wherein the value of a musical note is a quarter note when the molecular bond is a single bond, the value of a musical note is an eighth note when the molecular bond is a double bond, and the value of a musical note is a sixteenth note when the molecular bond is a triple bond.

7. The method of claim 1, wherein each element of the molecule is associated with an element group in a plurality of periodic table element groups, wherein each semitone in a set of semitones of a chromatic scale is associated with a class of music notes, wherein elements from a same group are mapped in a same class of music notes.

8. The method of claim 1, further comprising:
   detecting a presence of a particular molecule; and
   alerting as to the presence of the particular molecule.

9. An electronic music device comprising:
   a memory comprising a database of rules governing mapping each element of a molecule to a musical note;
   a processor electronically coupled to the memory, the processor:
      mapping each element of a molecule to a musical note;
      determining a value of each musical note based upon a type of molecular bond between elements; and
      arranging the musical notes in a sequence; and
   a speaker electronically coupled to the processor, the speaker for playing the sequence of musical notes.

10. A computer program product for playing a representation of a molecule on an electronic musical device, the computer program product comprising a computer readable storage medium having program instructions embodied therewith, the program instructions executable by the electronic musical device to cause the electronic musical device to perform a method comprising:
   mapping each element of a molecule to a musical note;
   determining a value of each musical note based upon a type of molecular bond between elements;
   arranging the musical notes in a sequence; and
   playing the sequence of musical notes through a speaker of the electronic musical device.

* * * * *